United States Patent [19]
de Nanteuil et al.

[11] Patent Number: 5,444,049

[45] Date of Patent: Aug. 22, 1995

[54] PEPTIDE COMPOUNDS DERIVED FROM BORONIC ACID

[75] Inventors: Guillaume de Nanteuil, Suresnes; Christine Lila, Viroflay; Michel Laubie, Vaucresson; Tony Verbeuren, Vernouillet; Serge Simonet, Conflans Sainte Honorine; Alain Rupin, Savonnieres; Bernard Portevin, Elancourt, all of France

[73] Assignee: Adir et Compagnie, Courbevoie, France

[21] Appl. No.: 199,473

[22] Filed: Feb. 22, 1994

[30] Foreign Application Priority Data

Feb. 24, 1993 [FR] France .................. 93 02082

[51] Int. Cl.$^6$ .................................. A61K 38/06
[52] U.S. Cl. ........................ 514/18; 514/19; 530/331; 562/7; 562/445
[58] Field of Search ............... 514/19, 18; 562/7; 530/331

[56] References Cited

FOREIGN PATENT DOCUMENTS 0293881  7/1988  European Pat. Off. ....... C07K 5/00

*Primary Examiner*—Jill Warden
*Assistant Examiner*—David Lukton
*Attorney, Agent, or Firm*—Gordon W. Hueschen

[57] ABSTRACT

A compound of formula (I):

$$R_1NH-\underset{R_2}{\underset{|}{C}}-CO-A-CO-NH-\underset{R_3}{\underset{|}{CH}}-B\underset{OR_5}{\overset{OR_4}{<}} \quad (I)$$

in which:

$R_1$ represents hydrogen or acyl, alkyl, benzyl, alkoxycarbonyl, benzyloxycarbonyl, phenoxycarbonyl, 5-[(dimethyl)amino]naphthylsulfonyl, alkoxycarbonylmethyl or carboxymethyl, $R_2$ represents hydrogen or phenyl, substituted or unsubstituted benzyl, 3-thienylmethyl, 2-pyridylmethyl, diphenylmethyl, fluorenyl, naphthylmethyl, benzocyclobutyl, (dicyclopropylmethyl)methyl, indanyl or ($C_3$-$C_7$ cycloalkyl)methyl, $R'_2$ represents hydrogen or benzyl or alternatively $R_2$ and $R'_2$ together represent $C_6H_5-CH=$, $R_3$ represents substituted alkyl or guanidinophenyl, amidinophenyl, aminophenyl, guanidinobenzyl, amidinobenzyl, aminobenzyl or cycloalkyl, $R_4$ and $R_5$ each represent hydrogen or alkyl, or $$B\underset{OR_5}{\overset{OR_4}{<}}$$

forms a boronic ester of pinanediol,

A represents any one of the groups as defined in the description.

Medicinal products.

12 Claims, No Drawings

PEPTIDE COMPOUNDS DERIVED FROM BORONIC ACID

The present invention relates to peptide compounds derived from boronic acid. One of these serine proteases, thrombin, is the key enzyme of coagulation, and has a pivotal role in the pathology of venous and arterial thromboses, as has been shown by F. Toti et al. (Sang, Thrombose, Vaisseaux, 4, 483–494, 1992) and T. M. REILLY et al. (Blood Coagulation and Fibrinolysis, 3, 513–517, 1992).

Antithrombotic approaches are more effective and are risk-free compared to the present treatments. Direct inhibitors of thrombin, which are currently undergoing clinical development, afford a whole series of advantages over heparin. However, these substances, hirudin and hirulog-1, have the disadvantage of not being active via the oral route.

Furthermore, it is known that peptides containing the sequence (D)Phe-Pro-Arg, present in fibrinogen, are inhibitors of the catalytic site of thrombin (C. KETTNER et al., J. Biol. Chem., 265 (30), 18289–18297, 1990).

Peptide compounds derived from boronic acid and displaying antithrombotic activity have already been described in the literature. This applies, more especially, to the compounds described in Patents EP 293,881 and EP 471,651. M. A. HUSSAIN et al. have, moreover, demonstrated that Ac-(D)Phe-Pro-Arg-boronic acid (DUP714) is a thrombin inhibitor (Peptides, 12, 1153–1154, 1991).

It was hence especially advantageous to synthesize new serine protease inhibitors in order to increase the potency and selectivity, as well as the activity via the oral route, of the compounds already described in the literature.

More specifically, the present invention relates to the compounds of formula (I):

$$R_1NH-\underset{\underset{R'_2}{\overset{R_2}{|}}}{C}-CO-A-CO-NH-\underset{\underset{R_3}{|}}{CH}-B\overset{OR_4}{\underset{OR_5}{\diagdown}} \quad (I)$$

in which:
R$_1$ represents a hydrogen atom or a linear or branched (C$_1$-C$_6$) acyl, linear or branched (C$_1$-C$_6$) alkyl, benzyl, linear or branched (C$_1$-C$_6$) alkoxycarbonyl, benzyloxycarbonyl, phenoxycarbonyl, 5-[(dimethyl)-amino]naphthylsulfonyl, alkoxycarbonylmethyl or carboxymethyl group, R$_2$ represents a hydrogen atom or one of the following groups:
  phenyl,
  benzyl (unsubstituted or substituted on the phenyl ring with one or more halogen atoms or linear or branched (C$_1$-C$_6$) alkyl, linear or branched (C$_1$-C$_6$) alkoxy, hydroxyl or bicyclooct-1-yl (unsubstituted or substituted with a hydroxyl or linear or branched (C$_1$-C$_6$) alkoxy group) groups),
  thienylmethyl,
  pyridylmethyl,
  diphenylmethyl,
  fluorenyl,
  naphthylmethyl,
  benzocyclobutyl,
  (dicyclopropylmethyl)methyl,
  indanyl, or
  (C$_3$-C$_7$ cycloalkyl)methyl, R'$_2$ represents a hydrogen atom or a benzyl group, or alternatively R$_2$ and R'$_2$ together represent C$_6$H$_5$—CH=, R$_3$ represents one of the following groups:
  linear or branched (C$_2$-C$_4$) alkyl substituted with a linear or branched (C$_1$-C$_6$) alkoxy, phenoxy, guanidino, amidino, amino, tetrahydro-2-furyl or (C$_3$-C$_7$) cycloalkyl group,
  guanidinophenyl, amidinophenyl, aminophenyl, guanidinobenzyl, amidinobenzyl, aminobenzyl, or (C$_3$-C$_7$) cycloalkyl, R$_4$ and R$_5$ each represent a hydrogen atom or a linear or branched (C$_1$-C$_6$) alkyl group, or $$B\overset{OR_4}{\underset{OR_5}{\diagdown}}$$

forms a boronic ester of pinanediol,
A represents either of the following groups:

$$*-\underset{\underset{A_1}{\diagdown\diagup}}{N}\!\!\!-\!\!\!-CH-$$

in which:
A$_1$, with the nitrogen and carbon atoms to which it is linked, represents a cyclic structure chosen from the following structures:
  perhydroindole,
  2-azabicyclo[2.2.2]octane,
  2-azabicyclo[3.3.0]octane,
  2-azabicyclo[2.2.1]heptane,
  perhydroisoindole,
  indoline,
  isoindoline,
  perhydroquinoline,
  perhydroisoquinoline,
  1,2,3,4-tetrahydroquinoline,
  1,2,3,4-tetrahydroisoquinoline,
  thiazolidine, optionally substituted with one or more linear or branched (C$_1$-C$_6$) alkyl groups,
or $$-\underset{\underset{A_2}{|}}{N}\!\!\!-\!\!\!-\underset{\underset{R_6\ \ R'_6}{}}{(C)_n}\!-\!$$

in which:
n represents 1 or 2,
R$_6$ represents a hydrogen atom or a (C$_3$-C$_7$) cycloalkyl, linear or branched (C$_1$-C$_6$) alkyl or carboxymethyl group,
R'$_6$ represents a hydrogen atom, or alternatively
R$_6$ and R'$_6$, with the carbon atom which carries them, form a (C$_3$-C$_7$) cycloalkyl group,
A$_2$ represents a linear or branched (C$_1$-C$_6$) alkyl, phenyl, indanyl, (C$_3$-C$_7$) cycloalkyl (unsubstituted or substituted with one or more methyl groups), cycloalkenyl (C$_3$-C$_7$), cyclopentadienyl, 2,2,2-trifluoro-1-cyclopentylethyl, bicyclo[2.1.1]hexyl, bicyclo[2.2.1]heptyl group or a group $$\underset{X \text{———} Y}{\diagup\hspace{-0.5em}\square\hspace{-0.5em}\diagdown} \quad 5$$

in which

X and Y, which are different, represent an oxygen or sulfur atom, an NH group or CH$_2$ group, or alternatively A$_2$ represents a hydrogen atom, (on condition that, in this case, R$_6$ represents a (C$_3$–C$_7$) cycloalkyl group and R'$_6$ represents a hydrogen atom or alternatively R$_6$ and R'$_6$, with the carbon atom which carries them, form a (C$_3$–C$_7$) cycloalkyl group), their enantiomers, diastereoisomers and epimers as well as their addition salts with a pharmaceutically acceptable acid or base.

The invention also relates to the process for preparing the compounds of formula (I), wherein a protected amino acid of formula (II), the isomers of which have been separated, where appropriate, by a standard separation technique:

$$R'_1\text{—NH—}\underset{R_2 \quad R'_2}{\overset{\diagup\quad\diagdown}{C}}\text{—CO}_2\text{H} \quad (II)$$

in which:

R'$_1$ represents a linear or branched (C$_1$–C$_6$) acyl, benzyl, linear or branched (C$_1$–C$_6$) alkoxycarbonyl, benzyloxycarbonyl or phenoxycarbonyl group, and R$_2$ and R'$_2$ have the same meaning as in the formula (I), is reacted according to the peptide coupling technique described by W. KONIG and R. GEIGER (Ber., 103, 788, 1970) with a second protected amino acid of formula (III), the isomers of which have been separated, where appropriate, according to a standard separation technique, $$HA\text{—CO}_2CH_2C_6H_5 \quad (III)$$

in which A has the same meaning as in the formula (I), to yield the compound of formula (IV):

$$R'_1\text{—NH—}\underset{R_2 \quad R'_2}{\overset{\diagup\quad\diagdown}{C}}\text{—CO—A—CO}_2CH_2C_6H_5 \quad (IV)$$

in which R'$_1$, R$_2$, R'$_2$ and A have the same meaning as above, the acid function of which is deprotected by catalytic hydrogenation to yield the compound of formula (V):

$$R'_1\text{—NH—}\underset{R_2 \quad R'_2}{\overset{\diagup\quad\diagdown}{C}}\text{—CO—A—CO}_2H \quad (V)$$

in which R'$_1$, R$_2$, R'$_2$ and A have the same meaning as above, which is reacted with N-hydroxysuccinimide in the presence 1,3-dicyclohexylcarbodiimide in an anhydrous medium, to yield the compound of formula (VI):

$$R'_1\text{—NH—}\underset{R_2 \quad R'_2}{\overset{\diagup\quad\diagdown}{C}}\text{—CO—A—CO}_2\text{—Suc} \quad (VI)$$

in which R'$_1$, R$_2$, R'$_2$ and A have the same meaning as above and Suc represents a succinimido radical, which is reacted in a basic medium with a compound of formula (VII):

$$H_2N\text{—CH—}\underset{R'_3}{\overset{\diagup O\text{—}R'_4}{B}}\diagdown O\text{—}R'_5 \quad (VII)$$

in which:

R'$_3$ represents one of the following groups:
linear or branched (C$_2$–C$_4$) alkyl substituted with a halogen atom or a linear or branched (C$_1$–C$_6$) alkoxy, phenoxy, tetrahydro-2-furyl or cycloalkyl group,
(C$_3$–C$_7$) cycloalkyl,
phenyl or benzyl, each being substituted with a halogen atom or a suitably protected amino group, R'$_4$ and R'$_5$ each represent a linear or branched (C$_1$–C$_6$) alkyl group, or $$B\underset{\diagdown OR'_5}{\diagup OR'_4}$$

forms a boronic ester or pinanediol, to yield:

either the compound of formula (I/a), a special case of the compounds of formula (I):

$$R'_1\text{—NH—}\underset{R_2 \quad R'_2}{\overset{\diagup\quad\diagdown}{C}}\text{—CO—A—CO—NH—}\underset{R'_{3a}}{\overset{|}{CH}}\text{—B}\underset{\diagdown OR'_5}{\diagup OR'_4} \quad (I/a)$$

in which R'$_1$, R$_2$, R'$_2$, A, R'$_4$ and R'$_5$ have the same meaning as above and R'$_{3a}$ represents a linear or branched (C$_2$–C$_4$) alkyl group (substituted with a linear or branched (C$_1$–C$_6$) alkoxy, phenoxy, tetrahydro-2-furyl or (C$_3$–C$_7$) cycloalkyl group) or a (C$_3$–C$_7$) cycloalkyl group, or the compound of formula (VIII):

$$R'_1\text{—NH—}\underset{R_2 \quad R'_2}{\overset{\diagup\quad\diagdown}{C}}\text{—CO—A—CO—NH—}\underset{R'_{3b}}{\overset{|}{CH}}\text{—B}\underset{\diagdown OR'_5}{\diagup OR'_4} \quad (VIII)$$

in which R'$_1$, R$_2$, R'$_2$, A, R'$_4$ and R'$_5$ have the same meaning as above and R'$_{3b}$ represents one of the following groups:
(C$_2$–C$_4$)alkyl substituted with a halogen atom,
phenyl or benzyl, each being substituted with a halogen atom or a suitably protected amino group, which compound of formula (VIII):
when R'$_{3b}$ represents one of the following groups:
alkyl substitued with a halogen atom,
phenyl or benzyl, each being substituted with a halogen atom, may be converted to the corresponding cyano compound by the action of copper cyanide, and hence the corresponding amidino compound of formula (I/b), a special case of the compounds of formula (I), by the action of aqueous ammonia:

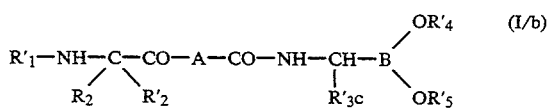

in which R'$_1$, R$_2$, R'$_2$, A, R'$_4$ and R'$_5$ have the same meaning as above and R'$_{3c}$ represents an alkyl, phenyl or benzyl group, each being substituted with an amidino group, when R'$_{3b}$ represents:

an alkyl group substituted with a halogen atom, may be converted to the corresponding azido compound by the action of sodium azide, and then by catalytic hydrogenation to the corresponding amino compound of formula (I/c), a special case of the compounds of formula (I), or a phenyl or benzyl group, each being substituted with a protected amino group, can undergo a deprotection to yield the compound of formula (I/c), a special case of the compounds of formula (I):

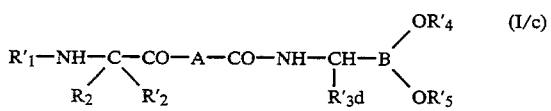

in which R'$_1$, R$_2$, R'$_2$, A, R'$_4$ and R'$_5$ have the same meaning as above and R'$_{3d}$ represents an alkyl, phenyl or benzyl group, each being substituted with an amino group, which compound of formula (I/c) may undergo conversion of the amino radical of the group R'$_{3d}$ therein to a guanidino radical by reaction with cyanamide, to yield the compound of formula (I/d), a special case of the compounds of formula (I):

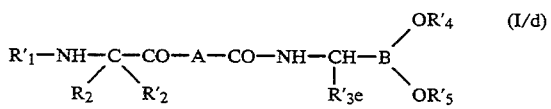

in which R'$_1$, R$_2$, R'$_2$, A, R'$_4$ and R'$_5$ have the same meaning as above and R'$_{3e}$ represents an alkyl, phenyl or benzyl group, each being substituted with a guanidino group, the terminal amine function of which compound of formula (I/a), (I/b), (I/c) or (I/d) is deprotected, if so desired, and which compound is converted, in an inert medium, using boron trichloride, to a boronic acid of formula (I/e) a special case of the compounds of formula (I):

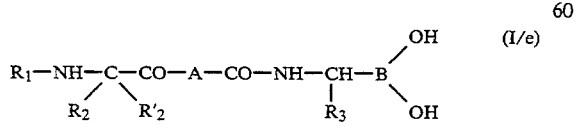

in which R$_1$, R$_2$, R'$_2$, A and R$_3$ have the same meaning as in the formula (I), which compound of formula (I/a), (I/b), (I/c), (I/d) or (I/e):

is optionally purified according to a standard purification technique, undergoes, if so desired, a separation of its enantiomers according to a standard separation technique, and which is converted, where appropriate, to its addition salts with a pharmaceutically acceptable acid or base.

Among pharmaceutically acceptable acids, there may be mentioned, without implied limitation, hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic, camphoric, oxalic, and the like, acids.

Among pharmaceutically acceptable bases, there may be mentioned, without implied limitation, sodium hydroxide, potassium hydroxide, sodium bicarbonate, and the like.

The compounds of formula (VII) are obtained:
either from the compound of formula (IX), obtained according to the process described by M. W. RATHKE et al. (J. Organomet. Chem., 122, 145–149, 1976):

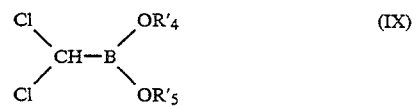

in which R'$_4$ and R'$_5$ are as defined above, which is reacted with an organomagnesium compound of formula (X):

in which R represents:
a linear or branched (C$_2$-C$_4$) alkyl group (substituted with a linear or branched (C$_1$-C$_6$) alkoxy, phenoxy, tetrahydro-2-furyl or (C$_5$-C$_7$) cycloalkyl group),
a (C$_3$-C$_7$) cycloalkyl group, or
a phenyl or benzyl group, each being substituted with a suitably protected amino group or with a halogen atom,
to yield the compound of formula (XI):

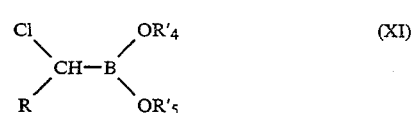

in which R, R'$_4$ and R'$_5$ are as defined above, which is reacted with 1,1,1,3,3,3-hexamethyldisilazane (HMDS) in the presence of n-butyllithium to yield, after treatment in an acid medium, the compound of formula (VII), or from an α-chlorinated boronic ester of formula (XII), prepared according to the process described by D. S. MATTESON et at. (Organometallics, 3, 1284–1288, 1984) and W. RATHKE et al., (J. Biol. Chem. 265 (30), 18289–18297, 1990):

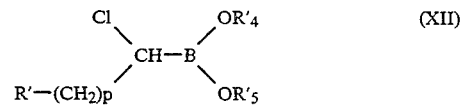

in which R'$_4$ and R'$_5$ are as defined above, p is an integer equal to 3 or 4 and R' represents a halogen atom or alkoxy group, which is reacted with 1,1,1,3,3,3-hexamethyldisilazane (HMDS) in the presence of n-butyllithium to yield, after treatment in an acid medium, the compound of formula (VII).

The compounds of the present invention, apart from being new, possess especially advantageous pharmacological properties.

They are potent inhibitors of trypsin-like serine proteases which display considerable selectivity with respect to thrombin compared to other serine proteases of coagulation. They possess, moreover, better activity via the oral route than the reference compound DUP 714.

These properties hence make them useful in the treatment of stable or unstable angina and of disorders of thrombotic origin and/or which give rise to thrombotic complications, as well as in the treatment or prevention of myocardial infarction and of venous or arterial thromboses.

They may also be used in therapeutic combination with a thrombolytic.

The invention also covers pharmaceutical compositions containing as active principle at least one compound of formula (I) with one or more suitable non-toxic, inert excipients. The pharmaceutical compositions thereby obtained may be presented in various forms, the most advantageous being tablets, dragées, hard gelatin capsules, suppositories, suspensions to be taken by mouth, and the like.

The appropriate dosage may be adapted according to the nature and severity of the complaint and the administration route, and also according to the patient's age and weight. This dosage varies from 1 to 500 mg per day, taken in one or several doses.

The examples which follow illustrate the invention but in no way limit it.

The starting materials used are known starting materials or are prepared according to known procedures.

Preparations A, B and C yield intermediates which are useful in the preparation of the compounds of the invention.

Preparation A: (+)-α-Pinanediol (R)-1-amino-4-bromobutylboronate hydrochloride

This compound was obtained according to the process described by C. KETTNER et at. (J. Biol. Chem., 265 (30), 18289–18297, 1990) by reacting allyl bromide with catecholborane, followed by a transesterification with (+)-α-pinanediol, then a homologation reaction in the presence of dichloromethyllithium and lastly a reaction with hexamethyldisilazane.

Melting point: 160° C. Optical rotation: $[\alpha]_D^{25} = +16.5°$ (c=1%, ethanol)

| | Elemental microanalysis: | | | |
|---|---|---|---|---|
| | C % | H % | N % | Cl % |
| calculated | 45.88 | 7.15 | 3.82 | 9.67 |
| found | 45.82 | 7.09 | 4.13 | 9.85 |

Preparation B: (+)-α-Pinanediol (R)-(1-amino-1-cyclopentyl)methylboronate, hydrochloride Stage A: (+)-α-Pinanediol dichloromethylboronate This compound was synthesized according to the process described by W. RATHKE et al. (J. Organomet. Chem., 122, 145–149, 1976) from dichloromethane and (+)-α-pinanediol, and is purified by vacuum distillation.

Boiling point: 125° C. (p=0.4 mmHg)

Stage B: (+)-α-Pinanediol (cyclopentyl)chloromethyl-boronate 4.75 mmol of cyclopentylmagnesium chloride are added dropwise to a solution, cooled to −78° C., containing 4.75 mmol of the compound obtained in the preceding stage in 7 ml of anhydrous tetrahydrofuran. The mixture is maintained for one hour at 0° C. and then, after a return to room temperature, the THF is evaporated off. The residue is taken up with an ether/water mixture and the ether phase is separated after settling has taken place, dried and evaporated to yield the expected product, which is purified by chromatography on a silica column using a pentane/dichloromethane (90:10) mixture as solvent.

Stage C: (+)-α-Pinanediol (R)-(1-amino-1-cyclopentyl)-methylboronate hydrochloride This compound was obtained according to the process described by C. KETTNER et al. (J. Biol. Chem., 2.65 (30), 18289–18297, 1990), using the compound described in the preceding stage.

Optical rotation: $[\alpha]_D^{21} = +13.4°$ (c=1%, methanol)

Preparation C: (+)-α-Pinanediol (R)-1-amino-4-methoxy-butylboronate hydrochloride Stage A: Allyl methyl ether 93 mmol of sodium methylate and 85 mmol of allyl bromide are stirred in a pressure bottle at room temperature for 12 hours. After cooling in dry ice, the expected product is obtained by distillation at atmospheric pressure.

Boiling point: B.p.=54°–55° C.

Stage B: 4-Methoxybutylcatecholborane 64 mmol of the product obtained in the preceding stage and 71.4 mmol of catecholborane are heated to reflux for 18 hours. The expected product is then obtained by distillation.

Boiling point: 80° C. (p=0.1 mmHg)

Stage C: (+)-α-Pinanediol 4-aminobutylboronate 20.5 mmol of the product obtained in the preceding stage are dissolved in 22 ml of anhydrous tetrahydrofuran. After cooling to 0° C., 20.5 mmol of (+)-α-pinanediol are added to the above mixture. The resulting mixture is left for 45 minutes at 5°–10° C. and then 45 minutes at room temperature. After evaporation of the solvent, 95 ml of hexane are added and the mixture is left overnight in a freezer. The ice-cold precipitate is then filtered off and washed with hexane. This precipitate, which converts to an oil at room temperature, is then distilled and yields the expected product.

Boiling point: 80° C. (p=0.01 mmHg)

Stage D: (+)-α-Pinanediol (R)-1-chloro-4-methoxybutyl-boronate

Stage E: (+)-α-Pinanediol (R)-1-amino-4-methoxybutyl-boronate hydrochloride

The products described in Stages D and E were obtained according to the process described by C. KETTNER et al., (J. Biol. Chem., 265 (30), 18289–18297).

The abbreviations used in the examples are as follows:

Ac represents acetyl,
Bz represents benzyl,
Suc represents the succinimido group,
(R)Phe represents the (R)-phenylalanyl residue,
Phi represents the (2S,3aS,7aS)-perhydro-2-indolecarbonyl residue,
Abo represents the (3S)-2-azabicyclo[2.2.2]octane-3-carbonyl residue,
Ala represents the alanyl residue, Gly represents the glycyl residue,
Clp represents the 1-aminocyclopentylcarbonyl residue of formula:

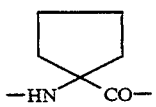

Asp represents the aspartyl residue,
βAla represents the β-alanyl residue,
Acn represents the 2-aminocinnamyl residue of formula:

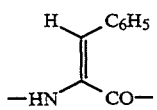

Example 1: (+)-α-Pinanediol
1-(R)-[(Ac-(RS)Phe-Phi)amino]-4-aminobutylboronate methanesulfonate Stage A: Ac-(RS)Phe-Phi-OBz Using the peptide coupling technique (DCC/IOBT) described by W. KONIG and R. GEIGER (Ber., 103, 788, 1970) and anhydrous dimethylformamide as the solvent, the expected product is prepared from 73 mmol of Phi-OBz and Ac-(R)Phe-OH and is purified by chromatography on a silica column using a dichloromethane/ethanol (97:3) mixture as eluent.

Yield: 76%

Stage B: Ac-(RS)Phe-Phi-OH 25 mmol of the product obtained in the preceding stage in 140 ml of ethanol are hydrogenated under a hydrogen pressure of 4 kg for 12 hours in the presence of 2 g of anhydrous palladium/C (10% Pd). After the catalyst has been filtered off, the expected product is obtained after evaporation of the solvent.

Yield: 97%

Stage C: Ac-(RS)Phe-Phi-OSuc 4.46 mmol of the product obtained in the preceding stage in 20 ml of anhydrous dichloromethane and then 4.46 mmol of dicyclohexylcarbodiimide dissolved in dichloromethane are added to 4.46 mmol of N-hydroxysuccinimide in 50 ml of anhydrous dichloromethane. The mixture is stirred for 12 hours at room temperature. After the dicyclohexylurea formed has been filtered off, the expected product is obtained after evaporation.

Stage D: (+)-α-Pinanediol 1-(R)-[(Ac-(RS)Phe-Phi)amino]-4-bromobutylboronate 1 mmol of the compound obtained in Preparation A in 10 ml of anhydrous dichloromethane and 1 mmol of the compound obtained in the preceding stage are placed under an argon atmosphere at −20° C. 14 ml of triethylamine are then added dropwise, and the mixture is maintained for 30 minutes at −20° C. After a return to room temperature, the mixture is stirred overnight under an argon atmosphere. After the product is taken up with ethyl acetate, the organic phase is washed with water, sodium bicarbonate, water, 0.2N hydrochloric acid and lastly water, dried and evaporated. The expected product is obtained after purification on "Sephadex".

Yield: 90%

Stage E: (+)-α-Pinanediol 1-(R)-[(Ac-(RS)Phe-Phi)amino]-4-azidobutylboronate 1.5 mmol of the product obtained in the preceding stage in 3 ml of anhydrous dimethylformamide are placed at 100 C. in the presence of 3 mmol of sodium azide for 4 hours. After 12 hours at room temperature, the mixture is taken up with an ethyl acetate/water mixture, and the organic phase is washed several times, dried and evaporated, and yields the expected product.

Yield: 95%

Stage F: (+)-α-Pinanediol 1-(R)-[(Ac-(RS)Phe-Phi)amino]-4-aminobutylboronate methanesulfonate 1.4 mmol of the compound obtained in the preceding stage in 25 ml of anhydrous methanol are hydrogenated for 2 hours in the presence of 1.4 mmol of methanesulfonic acid using 50 mg of palladium/C (10% Pd) as catalyst. After the catalyst has been filtered off and rinsed and the filtrate evaporated, the expected product is obtained.

Yield: 95%

Example 2: (+)-α-Pinanediol
1-(R)-[(Ac-(RS)Phe-Phi)amino]-4-guanidinobutylboronate methanesulfonate 1.3 mmol of the compound obtained in Example 1 and 10.3 mmol of cyanamide are brought to reflux in 8 ml of anhydrous ethanol for 10 days. After evaporation of the ethanol and passage through Sephadex medium taking up the residue with methanol, the expected product is obtained.

Yield: 91%

Example 3:
1-(R)-[(Ac-(RS)Phe-Phi)amino]-4-guanidinobutylboronic acid acetate 1.2 mmol of the compound obtained in Example 2 in 30 ml of anhydrous dichloromethane are cooled to −78° C. under an argon atmosphere. 4.8 mmol of boron trichloride are then added dropwise in the course of 30 minutes. The temperature is brought to 0° C. and the mixture is stirred for 30 minutes. 10 ml of ice-cold water are then added and, after 15 minutes of stirring, the mixture is brought to room temperature. The organic phase is separated after settling has taken place and extracted with 10 ml of a water/acetic acid (90:10) mixture. The remaining aqueous phase is washed with ether, and the combined aqueous phases are evaporated. The residue is purified on Bio-gel using a water/acetic acid (90:10) mixture as eluent, and yields the expected product, which is lyophilized.

| | Elemental microanalysis: | | |
|---|---|---|---|
| | C % | H % | N % |
| calculated | 56.45 | 7.54 | 14.63 |
| found | 54.71 | 7.26 | 13.59 |

Example 4:
1-(R)-[(Ac-(R)Phe-Phi)amino]-4-aminobutylboronic acid acetate

This compound was obtained according to the same process as that described in Example 3, using the compound of Example 1 as starting material.

Example 5: (+)α-Pinanediol
(R)-[(Ac-(R)Phe-Phi)amino]-cyclopentyl)methylboronate Stages A to C: These stages are identical to Stages A to C of Example 1.

Stage D:

This compound was obtained according to the process described in Stage D of Example 1, from the compound obtained in Stage C and the compound obtained in Preparation B.

Yield: 90%

Example 6:
(R)-[(Ac-(R)Phe-Phi)amino]cyclopentyl)methylboronic acid acetate

This compound was obtained according to the process described for Example 3, using the compound of Example 5 as starting material.

The compounds of Examples 7 to 14 were synthesized according to the same process as that described in Example 1, using the corresponding starting materials.

Example 7: (+)-α-Pinanediol 1-(R)-[(Ac-(RS)Phe-Abo)amino]-4-aminobutylboronate methanesulfonate Example 8: (+)-α-Pinanediol 1-(R)-{[(Ac-(R)-(cyclohexyl)Ala-(N-cyclopentyl)-Gly]amino}-4-aminobutylboronate methanesulfonate Example 9: (+)-α-Pinanediol 1-(R)-{[Ac-(R)Phe-(N-cyclobutyl)Gly]amino}-4-aminobutylboronate methanesulfonate Example 10: (+)-α-Pinanediol 1-(R)-{[Ac-(RS)Phe-(N-cyclohexyl)Gly]amino}-4-aminobutylboronate methanesulfonate Example 11: (+)-α-Pinanediol 1-(R)-{[Ac-(RS)Phe-(N-cyclopentyl)Gly]amino}-4-aminobutylboronate methanesulfonate Example 12: (+)-α-Pinanediol 1-(R)-{[Ac-(R)Phe-(N-cyclopentyl)Gly]amino}-4-aminobutylboronate methanesulfonate Example 13: (+)-α-Pinanediol 1-(R)-{[Ac-(S)Phe-(N-cyclopentyl)Gly]amino}-4-aminobutylboronate methanesulfonate Example 14: (+)-α-Pinanediol 1-(R)-{[Ac-(RS)Phe-(N-(RS)indan-1-yl)Gly]amino}-4-aminobutylboronate methanesulfonate Examples 15 to 22 were synthesized according to the same process as that described for Example 2, using the corresponding starting materials.

Example 15: (+)-α-Pinanediol 1-(R)-[(Ac-(RS)Phe-Abo)amino]-4-guanidinobutylboronate benzenesulfonate From the compound described in Example 7.

Example 16: (+)-α-Pinanediol 1-(R)-{[Ac-(R)-(cyclohexyl)Ala-(N-cyclopentyl)-Gly]amino}-4-guanidinobutylboronate benzenesulfonate From the compound of Example 8.

Example 17: (+)-α-Pinanediol 1-(R)-{[Ac-(R)Phe-(N-cyclobutyl)Gly]amino}-4-guanidinobutylboronate benzenesulfonate From the compound of Example 9.

Example 18: (+)-α-Pinanediol 1-(R)-{[Ac-(RS)Phe-(N-cyclohexyl)Gly]amino}-4-guanidinobutylboronate benzenesulfonate From the compound of Example 10. Mass spectrum: FAB+: [M+H]: m/z=636

Example 19: (+)-α-Pinanediol 1-(R)-{[Ac-(RS)Phe-(N-cyclopentyl)Gly]amino}-4-guanidinobutyl-boronate benzenesulfonate From the compound of Example 11. Mass spectrum: FAB+: [M+H]: m/z=622

Example 20: (+)-α-Pinanediol 1-(R)-{[Ac-(R)Phe-(N-cyclopentyl)Gly]amino}-4-guanidinobutylboronate trifluoroacetate From the compound of Example 12. Mass spectrum: FAB+: [M+H]: m/z=622

Example 21: (+)-α-Pinanediol 1-(R)-{[Ac-(S)Phe-(N-cyclopentyl)Gly]amino}-4-guanidinobutylboronate benzenesulfonate From the compound of Example 13.

Example 22: (+)-α-Pinanediol 1-(R)-{[Ac-(RS)Phe-(N-(RS)indan-1-yl)Gly]amino}-4-guanidinobutylboronate benzenesulfonate From the compound of Example 14.

Examples 23 to 30 were synthesized according to the same process as that described in Example 3, from the corresponding starting materials.

Example 23:
1-(R)-[(Ac-(RS)Phe-Abo)amino]-4-guanidinobutylboronic acid acetate

From the compound of Example 15. Mass Spectrum: FAB+: [M+glycerol-2H$_2$O+H]+: m/z=557

Example 24:
1-(R)-{[Ac-(R)-(cyclohexyl)Ala-(N-cyclopentyl)-Gly]amino}-4-guanidinobutyl boronic acid acetate From the compound of Example 16. Mass spectrum: FAB+: [M+glycerol-2H$_2$O+H]+: m/z=586

Example 25:
1-(R)-{[Ac-(R)Phe-(N-cyclobutyl)Gly]amino}-4-guanidinobutylboronic acid acetate From the compound of Example 17. Mass spectrum: FAB+: [M+glycerol-2H$_2$O+H]+: m/z=566

Example 26:
1-(R)-{[Ac-(RS)Phe-(N-cyclohexyl)Gly]-amino}-4-guanidinobutylboronic acid methanesulfonate From the compound of Example 18.

| | Elemental microanalysis: | | |
| --- | --- | --- | --- |
| | C % | H % | N % |
| calculated | 55.52 | 7.71 | 14.94 |
| found | 56.20 | 7.25 | 14.54 |

Example 27:
1-(R)-{[Ac-(RS)Phe-(N-cyclopentyl)Gly]amino}-4-guanidinobutylboronic acid acetate From the compound of Example 19. Mass spectrum: FAB+: [M+glycerol-2H$_2$O+H]+: m/z=580

Example 28:
1-(R)-{[Ac-(R)Phe-(N-cyclopentyl)Gly]amino}-4-guanidinobutylboronic acid acetate From the compound of Example 20. Mass spectrum: FAB+: [M+glycerol-2H₂O+H]+: m/z=580

Example 29:
1-(R)-{[Ac-(S)Phe-(N-cyclopentyl)Gly]-amino}-4-guanidinobutylboronic acid acetate From the compound of Example 21. Mass spectrum: FAB+: [M+glycerol-2H₂O+H]+: m/z=580

Example 30:
1-(R)-{[Ac-(RS)Phe-(N-(RS)indan-1-yl)-Gly]amino}-4-guanidinobutylboronic acid acetate From the compound of Example 22. Mass Spectrum: FAB+: [M+glycerol-2H₂O+H]+: m/z=593

Example 31: (+)-α-Pinanediol 1-(R)-[(Ac-(RS)Phe-Phi)-amino]-4-methoxybutylboronate This compound was synthesized according to the process described in Example 1 (Stages A to D), replacing in Stage D the compound obtained in Preparation A by the compound obtained in Preparation C.

| | Elemental microanalysis | | |
|---|---|---|---|
| | C % | H % | N % |
| calculated | 67.63 | 8.43 | 6.76 |
| found | 67.16 | 8.39 | 7.10 |

Example 32:
1-(R)-[(Ac-(RS))Phe-Phi)amino]-4-methoxybutylboronic acid

This compound was synthesized according to the process described in Example 3, from the compound described in Example 31. Mass spectrum: FAB+: [M+glycerol-H₂O+H]+: m/z=543

Example 33: (+)-α-Pinanediol 1-(R)-{[N-(5-dimethylamino-1-naphthalenesulfonyl)Gly-Phi]-amino}-4-aminobutylboronate benzenesulfonate Stages A to D:
These stages A to D are identical to Stages A to D of Example 1 but, in Stage A, Ac-(R)Phe-OH is replaced by Boc-Gly-OH.

Stage E: (+)-α-Pinanediol 1-(R)-[(Gly-Phi)amino]-4-bromobutylboronate trifluoroacetate 6.64 mmol of the product obtained in the preceding stage dissolved in 20 ml of dichloromethane at 0° C. are deprotected in the presence of 53 mmol of trifluoroacetic acid. After 1 hour of stirring, 24 hours at room temperature, evaporation of the solvent and drying, the expected product is obtained.

Stage F: (+)-α-Pinanediol 1-(R)-{[N-(5-dimethylamino-1-naphthalenesulfonyl)Gly-Phi]amino}-4-bromobutylboronate To 6.53 mmol of the compound obtained in the preceding stage dissolved in 100 ml of tetrahydrofuran and protected from light, 19.8 mmol of triethylamine are added. After 5 minutes of stirring, 6.6 mmol of dansyl chloride are added portionwise. After 4 hours of stirring, evaporation of the solvent, taking up of the residue with ethyl acetate, washing with sodium hydrogen carbonate and evaporation, the expected product is obtained after purification on a Sephadex LH-20 column using methanol as eluent.

Stages G and H:
These stages are identical to Stages E and F of Example 1 but, in Stage F, methanesulfonic acid is replaced by benzenesulfonic acid.

Example 34:
(+)-α-Pinanediol 1-(R)-{[N-(5-dimethylamino-1-naphthalenesulfonyl)Gly-Phi]-amino}-4-guanidinobutylboronate benzenesulfonate The expected product is obtained according to the process described in Example 2, from the compound of Example 33.

Mass spectrum: FAB+(I+): [M+H]+ m/z=750

Example 35:
-(R)-{[N-(5-Dimethylamino-1-naphthalenesulfonyl)Gly-Phi]amino}-4-guanidinobutylboronic acid diacetate The expected product is obtained according to the process described in Example 3, from the compound of Example 34.

Mass spectrum: FAB+(I+): [M+H-glycerol-H₂O]+ m/z=672

Examples 36 to 61 were synthesized according to the process described in Example 3, using the corresponding starting materials.

Example 36:
1-(R)-{[Ac-(R)Phe-(N-cyclopenta-2,4-dienyl)-Gly]amino}-4-guanidinobutylboronic acid acetate

Example 37:
1-(R)-{[Ac-(R)Phe(N-bicyclo[2.1.1]hex-5-yl)Gly]amino}-4-guanidinobutylboronic acid acetate

Example 38:
1-(R)-{[Ac-(R)Phe-(N-1,2-oxazolidin-3-yl)Gly]amino}-4-guanidinobutylboronic acid acetate

Example 39:
1-(R)-{[Ac-(R)Phe-(N-cyclopent-3-enyl)-Gly]amino}-4-guanidinobutylboronic acid acetate

Example 40:
1-(R)-{[Ac-(R)Phe-(N-cyclopent-2-enyl)-Gly]amino}-4-guanidinobutylboronic acid acetate

Example 41:
1-(R)-{[Ac-(R)Phe-(N-(1-methyl)cyclopentyl)-Gly]amino}-4-guanidinobutylboronic acid acetate

Example 42:
1-(R)-{[Ac-(R)Phe-(N-(3,5-dimethyl)cyclopentyl)-Gly]amino}-4-guanidinobutylboronic acid acetate

Example 43:
1-(R)-{[Ac-(R)Phe-(N-(2,2-dimethyl)cyclopentyl)-Gly]amino}-4-guanidinobutylboronic acid acetate

Example 44:
1-(R)-{[Ac-(R)Phe-(N-(1-cyclopentyl)2,2,2-trifluoroethyl)-Gly]amino}-4-guanidinobutylboronic acid acetate Example 45:
1-(R)-{[Ac-(R)Phe-(N-cyclopropyl)Gly]-amino}-4-guanidinobutylboronic acid acetate Example 46:
1-(R)-{[Ac-(R)Phe-(N-(3-methyl)cyclobutyl)-Gly]amino}-4-guanidinobutylboronic acid acetate Example 47:
1-(R)-{[Ac-(R)Phe-(N-(1-ethyl)propyl)Gly]amino}-4-guanidinobutylboronic acid acetate Example 48:
1-(R)-{[Ac-(R)(3-thienyl)Ala-(N-cyclopentyl)-Gly]amino}-4-guanidinobutylboronic acid acetate Example 49:
1-(R)-{[Ac-(R)(diphenyl)Ala-(N-cyclopentyl)-Gly]amino}-4-guanidinobutylboronic acid acetate Example 50:
1-(R)-{[(R)Phe-(N-cyclopentyl)Gly]amino}-4-guanidinobutylboronic acid acetate Example 51:
1-(R)-{[(N-Methyl)(R)Phe-(N-cyclopentyl)-Gly]amino}-4-guanidinobutylboronic acid acetate Example 52:
1-(R)-{[Ac-(R)(benzocyclobutyl)Gly-(N-cyclopentyl)-Gly]amino}-4-guanidinobutylboronic acid acetate Example 53:
1-(R)-{[(N-Methyl)-(R)-phenylGly-(N-cyclopentyl)-Gly]amino}-4-guanidinobutylboronic acid acetate Example 54:
1-(R)-{[(N-Methoxycarbonylmethyl)-(R)-Phe-(N-cyclopentyl)Gly]amino}-4-guanidinobutylboronic acid acetate Example 55:
1-(R)-{[Ac[di(phenylmethyl)]Gly-(N-cyclopentyl)-Gly]amino}-4-guanidinobutylboronic acid acetate Example 56:
1-(R)-{[Ac-(R)Phe-(cyclopentyl)Gly]amino}-4-guanidinobutylboronic acid acetate Example 57:
1-(R)-{[Ac-(R)Phe-Clp]-4-guanidinobutylboronic acid acetate Example 58:
1-(R)-{[Ac-(R)Phe-(N-cyclopentyl)Ala]amino}-4-guanidinobutylboronic acid acetate Example 59:
1-(R)-{[Ac-(R)Phe-(N-cyclopentyl)Asp]-amino}-4-guanidinobutylboronic acid acetate Example 60:
1-(R)-{[Ac-(R)Phe-(N-cyclopentyl)-$\beta$-Ala]}-amino}-4-guanidinobutylboronic acid acetate Example 61:
1-(R)-{[Ac-(Acn)-(N-cyclopentyl)Gly]-amino}-4-guanidinobutylboronic acid acetate

PHARMACOLOGICAL STUDY OF THE COMPOUNDS OF THE INVENTION

Example 62: Antithrombotic activity

The model of experimental thrombosis used is that of a venous thrombosis induced in male Wistar rats by ligation of the inferior vena cava below the left renal vein. The test animals are anesthetized by intraperitoneal administration of Brietal ® (methohexital sodium) at a dose of 1 mg/kg. Ligation is then carried out. The test product is injected intravenously 15 minutes before ligation. 25 minutes after ligation, the vein is excized and the clot is recovered and then weighed after transfer to an oven at 37° C. for 12 hours. The compounds of the invention were tested at doses of 0.1, 0.25 and 0.5 mg/kg and compared with DUP 714 used as reference compound. The results of this test show that the compounds of the invention permit a significant decrease in the weight of the clot, the decrease being as large as that observed on injection of the reference compound (DUP 714). At 0.25 mg/kg, the compounds of the invention inhibit formation of the clot by approximately 50%.

Example 63: Anticoagulant activity, measurement of the thrombin time in rats and humans In the presence of a standard quantity of thrombin, a normal plasma coagulates in a defined and constant time, termed the thrombin time (TT). Any prolongation of this time reflects an abnormality of fibrin formation (coagulation).

Sprague-Dawley rats are anesthetized with pentobarbital sodium (60 mg/kg i.p.), the carotid artery is catheterized and blood samples are taken into trisodium citrate solution (0.109M). A platelet-poor plasma is obtained by centrifugation of the blood samples (3000 g, 15 minutes). Samples of venous blood are also taken from humans at the bend of the arm. Anticoagulation of the samples and preparation of platelet-poor plasma are identical to those carried out with rat blood.

The thrombin time is obtained with Prest thrombin reagent and determined automatically using a coagulometer.

The antagonist or the solvent (10 $\mu$l) is added to the plasma (90 $\mu$l) and then incubated for 2 minutes at 37° C. 100 1 of thrombin are added as the chronometer is started.

Under these conditions, the TT values obtained in the control plasma are of the order of 30 seconds in rats and 20 seconds in humans. The activity of an antagonist is evaluated by its capacity to prolong this thrombin time relative to the control.

Under these conditions, the compounds of the invention permit a prolongation of the thrombin time of 50-fold and more. The effect of the inhibitors is measured, and the concentration which multiplies the thrombin time by 2 ($CTT_2$) is determined. The results are reproduced in the following table:

| Products | Rat $CTT_2$ ($\mu$M) | Man $CTT_2$ ($\mu$M) |
|---|---|---|
| Ex. 3 | 0.23 | 0.07 |
| Ex. 23 | 0.17 | 0.11 |
| Ex. 27 | — | 0.20 |
| Ex. 28 | — | 0.19 |
| Ref: DUP 714 | 0.32 | 0.18 |

Thus, with the compound of Example 23, the concentration required for doubling the thrombin time in rats is one half that obtained with the reference compound (DUP 714). With the compound of Example 3, the concentration required for doubling the thrombin time in humans is less by a factor of 2.5 than that obtained with the reference compound (DUP 714).

Example 64: Inhibition of thrombin and of the serine proteases of coagulation and of fibrinolysis To evaluate in vitro the inhibitory activity of the boro-arginine products with respect to human thrombin (Sigma, specific activity 3230 NIHU/mg), purified human fibrinogen (4 mM, Stago) (Fg) or the chromogenic substrate H-D-Phe-Pip-Arg-pNA (44 mM, S2238, Kabi) was added to a given quantity of thrombin (0.7 or 2 nM) incubated beforehand with or without the inhibitor under test (20° C., 10 minutes).

To evaluate in vitro the selectivity of these products with respect to different serine proteases of fibrinolysis and of coagulation, the same protocol was applied to purified human plasmin (2 nM, Stago), to purified human activated protein C (2 nM, Stago), to purified human activated factor X (2 nM, Stago), to tissue plasminogen activator (2 nM, Calbiochem), to purified human urokinase (2 nM, Sigma) and to purified human plasma kallikrein (2 nM, Calbiochem), using different peptidyl para-nitroanilides as substrate: <Glu-Phe-Lys-pNA (0.50 mM, S 2403, Kabi) for plasmin, N-Cbo-Arg-Gly-Arg-pNA (0.38 mM, S 2765, Kabi) for factor Xa, <Glu-Pro-Arg-pNa (0.52 mM, S 2366, Kabi) for activated protein C, H-D-Pro-Phe-Arg-pNa (0.45 mM, S 2302, Kabi) for kallikrein, H-D-Ile-Pro-Arg-pNA (0.48 mM, S 2288, Kabi), <Glu-Gly-Arg-pNA (0.56 mM, S 2444, Kabi).

Inhibitors, enzymes and substrates are diluted in the same buffer (0.01 mM phosphate buffer, pH 7.4, containing 0.12M sodium chloride and 0.05% of bovine serum albumin), and then distributed in a polystyrene microplate in a volume of 50 l.

The fibrin formed by thrombin or by the paranitroaniline liberated by the action of the serine protease is measured spectrophotometrically at 405 nm after 15 to 30 minutes of reaction at 20° C.

The table below gives the concentration of compound inhibiting the enzyme activity by 50% ($IC_{50}$) in the presence of the reference product (DUP 714) and of the compounds of Examples 25, 27 and 28, relative to the control without product. The results demonstrate that the compounds of Examples 25 and 28 are a more potent inhibitors of human thrombin than the reference compound with respect to human fibrinogen. The compounds of Examples 25, 27 and 28 possess greater selectivity with respect to the serine proteases of coagulation and of fibrinolysis than reference compound DUP 714.

a restraining cage and 1.5 $cm^3$ of arterial blood are withdrawn into 0.109M citrate (1/9).

1 hour after the animal has awoken, the test products are administered orally at a single dose of 10 mg/kg.

Arterial blood samples (1.5 ml) are then withdrawn at 30 minutes, 60 minutes and 2 hours.

As each sample is withdrawn, 1.5 ml of physio-logical solution are reinjected into the animals.

The blood tubes are centrifuged for 15 minutes at 3000 g for preparation of the plasma. The time of onset of the coagulation phenomenon is measured after adding Prest thrombin.

The compounds of the invention increase the thrombin time (TT) in a dose-dependent manner, and their activity is equal to or greater than that obtained with the reference compound (DUP 714) during the first 2 hours. The results are reproduced in the following table, and show the factors by which the thrombin time is increased.

|  | Time (hours) | | |
| --- | --- | --- | --- |
| Product | 0.5 | 1 | 2 |
| DUP 714 | 4.0 | 3.7 | 3.9 |
| Ex. 3 | 7.7 | 7.1 | 5.6 |

Example 66: Measurement of anticoagulant activity ex vivo. Intravenous (i.v.) administration of the products OFA rats, fasted or otherwise, are anesthetized with pentobarbital (60 mg/kg i.p.). The carotid artery and the jugular vein are exposed and catheterized. The catheters are flushed with citrated (1/40) physiological solution. After installation of the catheters, a sample of 1.5 $cm^3$ of arterial blood is withdrawn into 0.109M citrate (1/9).

30 minutes later, the test product is administered i.v. in a volume of 1 ml.

Arterial blood samples (1.5 ml) are then withdrawn at 1 minute 30 sec and 5, 15, 30 and 60 minutes.

As each sample is withdrawn, 1.5 ml of citrated physiological solution are reinjected into the animal via the carotid.

The blood tubes are centrifuged for 15 minutes at 3000 g (preparation of plasma). 100 μl of plasma are incubated with 100 gl of activated cephalin. The time of onset of the coagulation phenomenon is measured after adding 100 μl of calcium.

The compounds of the invention, tested at a dose of

| Example | $IC_{50}$ (nM) | | | | | | | |
| --- | --- | --- | --- | --- | --- | --- | --- | --- |
|  | Thrombin | | | | | | | |
|  | Fg | S2238 | Plasmin | tPA | Urokinase | FXa | Kalli | PCa |
| Ref. DUP 714 | 0.55 | 2.0 | 28 | 8 | 24 | 41 | 8 | 17 |
| Ex. 28 | 0.46 | 2.0 | 445 | 47 | 1821 | 225 | 91 | 82 |
| Ex. 25 | 0.45 | 2.0 | 818 | 14 | 1636 | 356 | 75 | 211 |
| Ex. 27 | 0.79 | 2.5 | 735 | 38 | 3176 | 1757 | 104 | 149 |

Example 65: Measurement of anticoagulant activity ex vivo. Oral administration of the products (conscious rats)

Fasted OFA rats are anesthetized with ether. The cordal artery is exposed and catheterized. The catheter is flushed with citrated (1/40) physiological solution. After installation of the catheter, the animal is placed in 0.5 mg/kg, increase the activated cephalin time (ACT) in a dose-dependent manner. The effect is comparable to or greater than that of the reference compound (DUP 714). The increase in ACT noted with the compounds of the invention is still significant 60 minutes after their administration. The results are reproduced in the following table, and show the factors by which the coagulation time is increased.

| Product | Time (min) | | | | |
| --- | --- | --- | --- | --- | --- |
|  | 15.5 | 5 | 15 | 30 | 60 |
| DUP 714 | 7.6 | 3.4 | 2.0 | 1.7 | 1.4 |
| Ex. 3 | 7.3 | 4.7 | 3.6 | 2.6 | 2.0 |
| Ex. 27 | 5 | 2.3 | 1.7 | 1.5 | 1.3 |

Example 67: Anticoagulant activity and thrombopenia p.o. in dogs

The products were administered orally to dogs. 2 hours and 4 hours after the treatment, and blood was withdrawn via the intravenous route. The plasma is prepared, platelets counted and the thrombin time test is carried out. The table demonstrates that DUP 714 at a concentration of 2.5 mg/kg has increased TT but caused a marked thrombopenia. The products of the invention at a concentration of 5 mg/kg has caused larger increases in the TT than DUP 714 without modifying the platelet count.

|  |  | Increase factor TT | Change in platelet count (% of control) |
| --- | --- | --- | --- |
| Ref. DUP 714 | 2 hr | 7 | −32% |
| (2.5 mg/kg) | 4 hr | 2 | −16% |
| Ex. 27 | 2 hr | 11 | −4% |
| (5 mg/kg) | 4 hr | 3 | −1% |
| Ex. 28 | 2 hr | 11 | −4% |
| (5 mg/kg) | 4 hr | 2 | +1% |

PHARMACEUTICAL COMPOSITION

Example 68: Pharmaceutical composition

Preparation formula for 1000 tablets containing a 10 mg dose:

| Compound of Example 3 | 10 g |
| --- | --- |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula(I):

$$R_1NH-\underset{\underset{R_2}{|}}{\overset{\overset{R'_2}{|}}{C}}-CO-A-CO-NH-\underset{\underset{R_3}{|}}{CH}-B\underset{OR_5}{\overset{OR_4}{<}} \quad (I)$$

in which:

R$_1$ represents hydrogen or linear or branched (C$_1$-C$_6$) acyl, benzyl, linear or branched (C$_1$-C$_6$) alkoxycarbonyl, benzyloxycarbonyl, or phenoxycarbonyl, R$_2$ represents hydrogen or one of the following groups:
  benzyl (unsubstituted or substituted on the phenyl ring with one or more halogen or linear or branched (C$_1$-C$_6$) alkyl, linear or branched (C$_1$-C$_6$) alkoxy, hydroxyl or bicycloct-1-yl (unsubstituted or substituted with hydroxyl or linear or branched (C$_1$-C$_6$) alkoxy)),
  diphenylmethyl,
  naphthylmethyl,
  (dicyclopropylmethyl)methyl,
  indanyl, or
  (C$_3$-C$_7$ cycloalkyl)methyl, R'$_2$ represents hydrogen R$_3$ represents one of the following groups:
  linear or branched (C$_2$-C$_4$) alkyl substituted with linear or branched (C$_1$-C$_6$) alkoxy, guanidino, or amino,
  (C$_3$-C$_7$) cycloalkyl, R$_4$ and R$_5$ each represent hydrogen or linear or branched (C$_1$-C$_6$) alkyl, or $$B\underset{OR_5}{\overset{OR_4}{<}}$$

forms a boronic ester of pinanediol,

A represents one of the following groups:

$$*-\underset{\underset{A_1}{\diagdown \diagup}}{N}\text{————}CH-$$

in which

A$_1$, with the nitrogen and carbon atoms to which it is linked, represents a cyclic structure chosen from the following structures:
  perhydroindole,
  2-azabicyclo[2.2.2]octane,
  2-azabicyclo[3.3.0]octane,
  2-azabicyclo[2.2.1]heptane,
  perhydroisoindole,
  indoline,
  isoindoline,
  perhydroquinoline,
  perhydroisoquinoline,
  1,2,3,4-tetrahydroquinoline,
  1,2,3,4-tetrahydroisoquinoline,
  thiazolidine, optionally substituted with one or more linear or branched (C$_1$-C$_6$) alkyl, or $$-\underset{\underset{A_2}{|}}{N}\text{————}\underset{R_6\quad R'_6}{(C)_n}-$$

in which:

n represents 1 or 2,

R$_6$ represents hydrogen

R'$_6$ represents hydrogen, or alternatively

A$_2$ represents indanyl, (C$_3$-C$_7$) cycloalkyl (unsubstituted or substituted with one or more methyl), its enantiomers, diastereoisomers and epimers as well as its addition salts with a pharmaceutically-acceptable acid or base.

2. A compound of claim 1 in which R$_1$ represents acetyl, its enantiomers, diastereoisomers and epimers as well as its addition salts with a pharmaceutically-acceptable acid or base.

3. A compound of claim 1 in which R$_2$ represents benzyl, its enantiomers, diastereoisomers and epimers as well as its addition salts with a pharmaceutically-acceptable acid or base.

4. A compound of claim 1 in which A represents a group

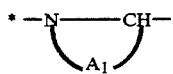

as defined in claim 1, its enantiomers, diastereoisomers and epimers as well as its addition salts with a pharmaceutically-acceptable acid or base.

5. A compound of claim 1 in which A represents a group

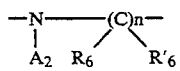

as defined in claim 1, its enantiomers, diastereoisomers and epimers as well as its addition salts with a pharmaceutically-acceptable acid or base.

6. A compound of claim 4 in which $A_1$, with the nitrogen and carbon atoms to which it is linked, represents a perhydroindole ring-system, its enantiomers, diastereoisomers and epimers as well as its addition salts with a pharmaceutically-acceptable acid or base.

7. A compound of claim 1 in which $R_3$ represents guanidino(linear or branched $(C_2-C_4)$alkyl, its enantiomers, diastereoisomers and epimers as well as its addition salts with a pharmaceutically-acceptable acid or base.

8. A compound of claim 1 in which $R_3$ represents $(C_3-C_7)$ cycloalkyl, its enantiomers, diastereoisomers and epimers as well as its addition salts with a pharmaceutically-acceptable acid or base.

9. The compound of claim 1 which is 1-(R)-[(Ac-(R)Phe-Phi)amino]-4-guanidinobutylboronic acid, Ac representing acetyl, (R)Phe representing (R)-phenylalanyl, Phi representing (2S,3aS,7aS)-perhydro-2-indolecarbonyl, and its isomers as well as its addition salts with a pharmaceutically-acceptable acid or base.

10. The compound of claim 1 which is 1-(R)-{[Ac-Phe-(N-cyclopentyl)Gly]amino}-4-guanidinobutylboronic acid acetate, Ac representing acetyl, Phe representing phenylalanyl of (RS) or (R) configuration, Gly representing glycyl, and its enantiomers as well as its addition salts with a pharmaceutically-acceptable acid or base.

11. A method for treating a mammal afflicted with a condition requiring an anti-thrombotic agent comprising the step of administering to the mammal an amount of a compound of claim 1 which is effective for alleviation of said condition.

12. A pharmaceutical composition useful as an anti-thrombotic agent comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,444,049
DATED : August 22, 1995
INVENTOR(S) : Guillaume de Nanteuil, et al It is certified that error appears in the above-indentified patent and that said Letters Patent is hereby corrected as shown below:

Column 8, line 20, "2.65" should read --265--.
Column 9, line 26, "/IOBT)" should read --/HOBT)--.
Column 10, line 26, A "Comma" should be inserted after --medium--.
Column 14, line 19, Add "1" to beginning of line.
Column 14, line 37, (approx.): Add "yl)-" to end of line.
Column 14, line 38, Delete "yl)" from beginning of line.
Column 14, line 42, (approx.): Add "yl)-" to end of line.
Column 14, line 43, Delete "yl)" from beginning of line.
Column 18, line 46, "gl" should read -- µl --.
Column 19, line 63, Add a "," after "hydroxyl".
Column 20, line 52, Line should be "underscored".
Column 22, line 7, "The" should read --A--.
Column 22, line 7, "selected from" should be inserted after "is".
Column 22, line 13, "The" should read --A--.
Column 22, line 13, "selected from" should be inserted after "is".

Signed and Sealed this

Twenty-eighth Day of November 1995

Attest:

BRUCE LEHMAN

*Attesting Officer*  *Commissioner of Patents and Trademarks*